(12) United States Patent
Garruzzo et al.

(10) Patent No.: US 10,796,550 B2
(45) Date of Patent: Oct. 6, 2020

(54) SYSTEM FOR MONITORING THE PHYSICAL CONDITION OF AT LEAST ONE USER AND METHOD FOR MONITORING THE PHYSICAL CONDITION OF A USER

(71) Applicants: Massimiliano Garruzzo, San Germano Chisone (IT); Marco Mattesi, Buttigliera Alta (IT); Ilario Sacchi, Turin (IT)

(72) Inventors: Massimiliano Garruzzo, San Germano Chisone (IT); Marco Mattesi, Buttigliera Alta (IT); Ilario Sacchi, Turin (IT)

( * ) Notice: Subject to any disclaimer, the term of this patent is extended or adjusted under 35 U.S.C. 154(b) by 0 days.

(21) Appl. No.: 16/333,859

(22) PCT Filed: Sep. 14, 2017

(86) PCT No.: PCT/IB2017/055549
§ 371 (c)(1),
(2) Date: Mar. 15, 2019

(87) PCT Pub. No.: WO2018/055485
PCT Pub. Date: Mar. 29, 2018

(65) Prior Publication Data
US 2019/0266873 A1 Aug. 29, 2019

(30) Foreign Application Priority Data
Sep. 20, 2016 (IT) .......................... 102016000094345

(51) Int. Cl.
*A61B 5/0402* (2006.01)
*G08B 7/06* (2006.01)
(Continued)

(52) U.S. Cl.
CPC ........ *G08B 21/0446* (2013.01); *A61B 5/0022* (2013.01); *A61B 5/0024* (2013.01);
(Continued)

(58) Field of Classification Search
CPC .................................................... A61B 5/0006
See application file for complete search history.

(56) References Cited

U.S. PATENT DOCUMENTS

2008/0300572 A1\* 12/2008 Rankers ............. A61B 5/14532
604/504
2009/0106045 A1\* 4/2009 Bae ........................ G06Q 50/22
705/2
(Continued)

FOREIGN PATENT DOCUMENTS

WO 2006119344 11/2006

*Primary Examiner* — Joseph H Feild
*Assistant Examiner* — Pameshanand Mahase
(74) *Attorney, Agent, or Firm* — Allen, Dyer, Doppelt + Gilchrist, P.A.

(57) ABSTRACT

Monitoring system of the physical condition of at least one user comprising at least one data detection device suitable to detect, by means of sensors, one or more indication data of the physical condition of the user and capable of sending said indication data to a data processing device; said data processing device being able to acquire and process the indication data received from said data detection device and able to compare such data with a range of predefined values and emitting an alarm signal when the received indication data do not fall within a range of predefined values.

14 Claims, 4 Drawing Sheets

(51) Int. Cl.
  *G08B 21/22* (2006.01)
  *G08B 21/04* (2006.01)
  *G08B 21/02* (2006.01)
  *A61B 5/00* (2006.01)
  *G08B 25/00* (2006.01)
  *G08B 25/01* (2006.01)
(52) U.S. Cl.
  CPC ............ *A61B 5/0402* (2013.01); *A61B 5/746* (2013.01); *G08B 7/06* (2013.01); *G08B 21/0277* (2013.01); *G08B 21/0283* (2013.01); *G08B 21/043* (2013.01); *G08B 21/0453* (2013.01); *G08B 21/0461* (2013.01); *G08B 25/001* (2013.01); *G08B 25/009* (2013.01); *G08B 25/016* (2013.01); *A61B 5/681* (2013.01); *A61B 5/6897* (2013.01)

(56) References Cited

U.S. PATENT DOCUMENTS

| | | | | |
|---|---|---|---|---|
| 2009/0322513 A1* | 12/2009 | Hwang | ............. | A61B 5/02055 340/539.12 |
| 2013/0241728 A1* | 9/2013 | Spector | ............. | G08B 21/0453 340/539.12 |
| 2013/0300559 A1 | 11/2013 | Chien et al. | | |
| 2015/0173674 A1* | 6/2015 | Hayes | ................... | A61B 5/681 600/301 |

* cited by examiner

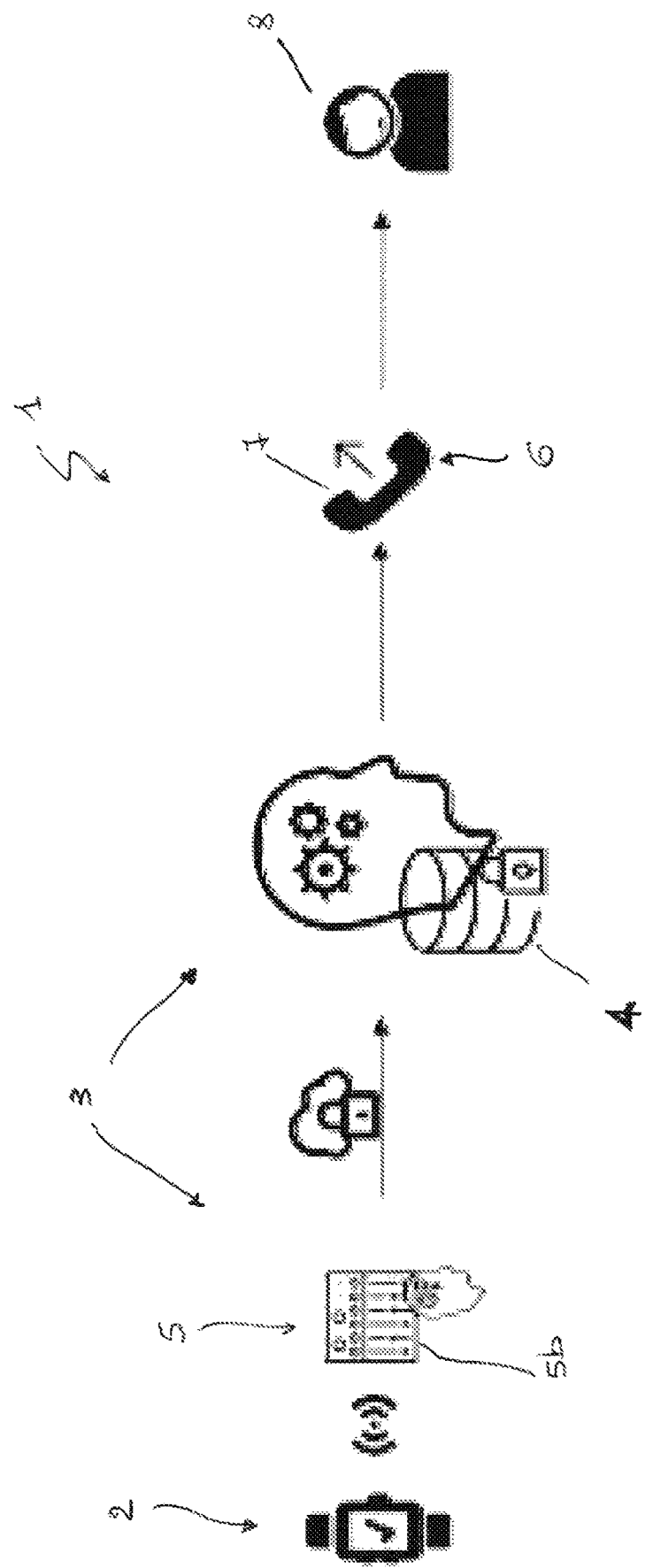

SYSTEM FOR MONITORING THE PHYSICAL CONDITION OF AT LEAST ONE USER AND METHOD FOR MONITORING THE PHYSICAL CONDITION OF A USER

The present invention relates to a system for monitoring the physical condition of at least one user and a method related thereto.

The present invention is particularly useful for all those users who require constant monitoring of their physical condition in order to receive immediate assistance in the event of danger.

Such a system may, for example, be advantageously used by insurance companies to monitor their insured clients and provide them with immediate assistance so as to offer additional service that, in addition to avoiding situations of serious danger to health or even life, also reduce possible damages.

Currently known life-saving devices are equipped with a portable device capable of communicating with an operations centre or with one or more rescuers to send an alarm signal.

If the user needs help, because he/she is not feeling well or is in danger, he/she activates the intervention request signal by pressing a button on the device.

The device is connected to a telephone switchboard that sends a voice call with a pre-recorded rescue message to one or more pre-set phone numbers (for example of a relative or friend who can administer first aid) or to an operations centre which, following a rescue protocol, activates emergency procedures.

The operations centre is notified of the intervention request and immediately contacts the emergency services, requesting the intervention of ambulances and medical personnel.

However, this system is not able to send rescue signals if the user does not activate the emergency signal himself/herself.

In other words, if the user does not activate the device in time, for example, following a sudden indisposition, the first aid procedures cannot be activated.

There are also devices that allow the user, via a webcam and a microphone, to send medical parameters at a distance so that medical staff can monitor the health of the user remotely and provide specialized medical assistance.

This type of device also still requires the intervention of the user who must enter and send his/her own parameters or autonomously use medical instrumentation (such as a sphygmomanometer, saturimeter, ECG or the like), which communicates with a medical centre.

Currently known devices have the limit of necessarily requiring active intervention by the user, not allowing assistance in case of sudden indisposition or accident. In other words, the rescue device is ineffective if the user is unable to send the rescue request autonomously.

The object of the present invention is to overcome the drawbacks encountered in the prior art.

In fact, one object of the present invention is to provide a system for monitoring the physical condition of a user, which allows rescue intervention even in case of sudden indisposition and/or accident.

Another object of the present invention is to provide a system for monitoring the physical condition of a user, which allows constant control of the biomedical parameters of said user, enabling rapid and immediate intervention in case of indisposition, accident or any other situation of danger.

It is also an object of the present invention to provide a method for monitoring the physical condition of a user, which allows rescue intervention without said user having to take an active part therein.

Further advantageous features are set forth in the appended claims.

The present invention will become more apparent from the detailed description that follows, with reference to the accompanying drawings provided purely by way of example, in which:

FIG. 2 is a schematic view of a system for monitoring the physical condition of a user according to the present invention in accordance with a second embodiment;

In the attached figures, the numeral 1 schematically indicates a system for monitoring the physical condition of at least one user in accordance with the present invention.

The monitoring system 1 comprises at least one data detection device 2 adapted to detect, by means of a plurality of detection sensors, not shown, positioned in the proximity of the user's body, one or more indicators of the user's physical condition.

Advantageously, the sensors are of the biometric type and are controlled by a microprocessor system.

Figures 3A, 3B:
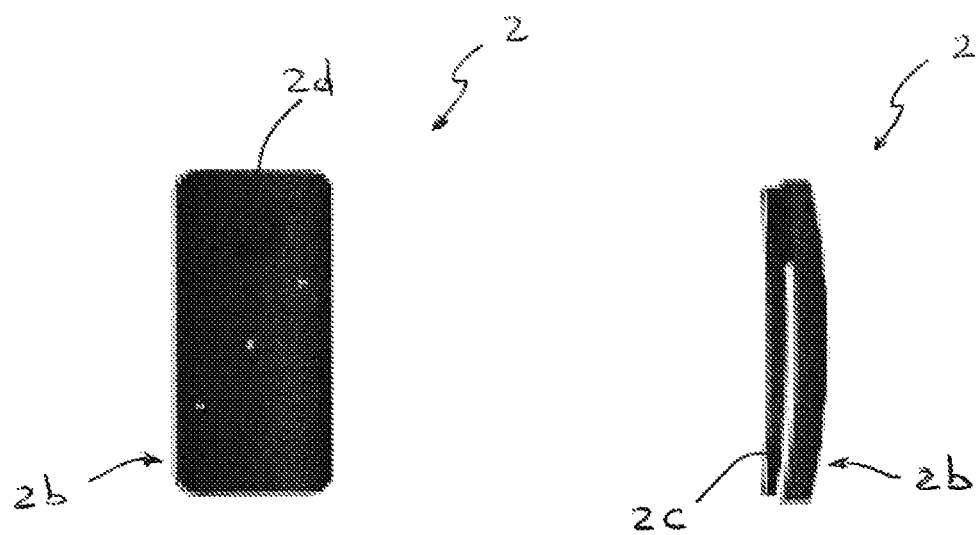
FIGS. 3a, 3b are a front view and a side view, respectively, of a data detection device forming the monitoring system object of the present invention according to a first embodiment.
Figures 4A, 4B:
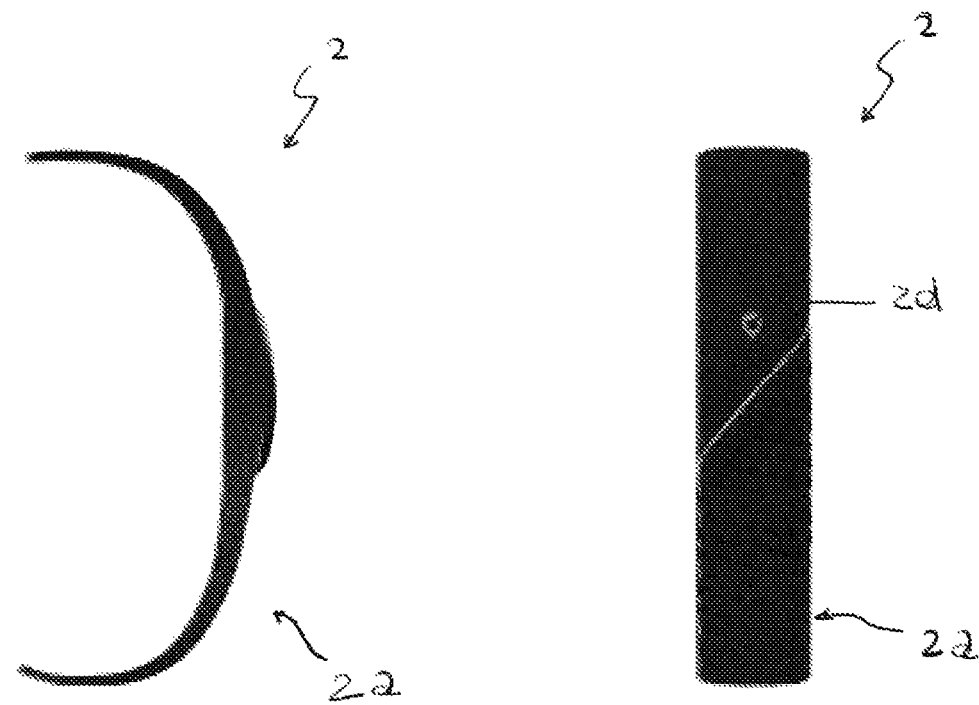
FIGS. 4a, 4b are a front view and a side view, respectively, of a data detection device forming the monitoring system object of the present invention according to a second embodiment.

The data detection device 2 is preferably of the wearable type and is in the form of a cuff 2a to be fastened to the body of the user (FIGS. 4a, 4b) or comprises a clip fastening element 2b (FIGS. 3a, 3b) suitable to fasten the wearable data detection device 2 to a garment of the user. In other words, the data detection device 2 comprises a detachable electronic module to be inserted in a cuff-like support 2a or provided with a clip 2c.

Preferably, the cuff 2a can be adjusted to any size of wrist and provide a closure that makes the fastening and tightening and untightening easy. Advantageously, the cuff will also be made of an anallergic, non-toxic material suitable for approval in the medical sector. It is also preferably ergonomic in order to allow the user to wear it around the clock.

In both of the above-mentioned embodiments, the data detection device 2 is equipped, for example, with a presence sensor, skin temperature sensor, plethysmography or heart rate sensor, and three-axis accelerometer.

Other types of sensors, such as for example a saturimeter (blood oxygenation) and radio frequency transmission. In addition to the Bluetooth Low Energy (BLE) transmission used in the basic versions, may be present in the most advanced versions.

The monitoring system 1 also comprises a data processing device 3, capable of acquiring and processing the indicators received from the data detection device 2. The data sent by the data detection device 2 to the data processing device 3 is compared by the latter with a predetermined range of values previously sent by the data detection device 2 as will be explained below.

The data processing device 3 is able to output an alarm signal when the indicators received are not within the predetermined range of values.

The measurements made by the data detection device 2 are made available through a wireless communication channel with the Bluetooth Low Energy (BLE) protocol or by radio frequency.

User interaction occurs through visual and sound signalling, as well as through a single multifunction button. Signalling may also be provided through a vibration device. There may also not be any type of display.

The data processing device 3 comprises a data acquisition control unit 4, or server.

The data processing device 3 may further comprise a communication device 5 capable of sending indicators to the data acquisition control unit 4.

The communication device 5 communicates with the data acquisition control unit 4 by sending the indicators or functional parameters of the user detected by the sensors present in the wearable data detection device 2.

The data acquisition control unit 4, or server processes the data received and compares it with preset values entered by the user or automatically recorded by the wearable data detection device 2.

For example, the heart rate data is read as "beat beat", and at each beat all data from all sensors is passed into a string to the data processing device 3.

It is also possible to enter one's own life-saving data, such as blood group, age, allergies, need for medication, etc., and keep the same as reference parameters: when the parameters detected by the data detection device 2 differ from the preset ones, the data processing device 3, in particular the data acquisition control unit 4, may decide to send the alarm signal to an operations centre 6 in order to activate one or more predetermined actions.

The operations centre 6, in response to the alarm signal sent by the data acquisition control unit 4, activates an alarm device 7. The latter is able in turn to send call signals to one or more predetermined communications devices.

The alarm device 7 is capable of emitting visual and/or acoustic warning signals to alert the user of an alarm signal. In other words, the alarm device 7 can give feedback to the monitored user about the triggering of an alarm that will be handled. The feedback is also used to prevent any false positive signals that could trigger a rescue without a real reason.

The data detection device 2 communicates with the data processing device 3 via a Bluetooth or Radio Frequency Transmission System.

The communication device 5 may include a personal communication device 5a, such as a mobile phone, computer, tablet or other media capable of receiving, handling and sending data received from the portable or wearable data detection device 2.

Alternatively, the communication device 5 may comprise a multiple communication device 5b, such as a station. "Multiple communication device" 5b is intended to mean a communication device capable of handling and communicating unidirectionally with a plurality of data detection devices 2 from which it receives input indicators.

In other words, in an alternative version, the monitoring system object of the present invention provides a plurality of data detection devices 2, each assigned to a respective user, and each adapted to detect, by means of sensors, one or more indicators of the physical condition of the corresponding user and able to send the detected indicators to a data processing device 3.

In both cases, therefore, with a single monitored user as well as with a plurality of users, the data processing device 3 acquires and processes the indicators received from the data detection device 2 of a single user or of each user and compares them with a predetermined range of values, corresponding to the respective user, outputting an alarm signal when the received indicators are not within the predetermined range of values for that specific user.

The wearable data detection device 2 sends the data to the communication device 5 (smartphone, tablet, computer, station) which performs a first processing, cross-references the data with the GPS positioning and, in the case of a pre-alarm, sends the data, preferably encrypted, to the data acquisition control unit 4, where an algorithm discriminates whether there is a danger or not, and in the positive case sends the call to the preset number to call in case of emergency (ICE) or to the operations centre that will call the user and, following a protocol, decide whether to end the call or inform the emergency services 8 such as the police or ambulance or fire brigade or whoever is responsible for handling the problem.

Figure 1:
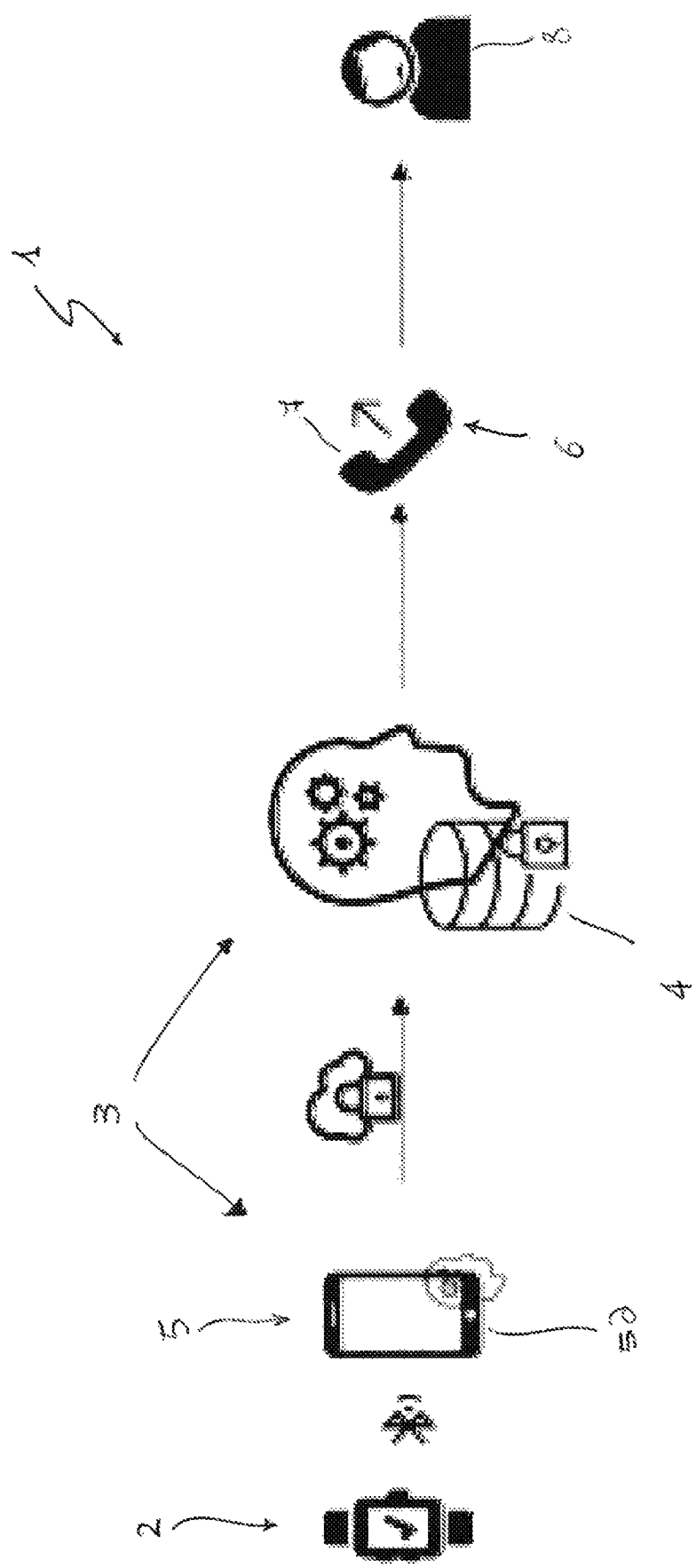
FIG. 1 is a schematic view of a system for monitoring the physical condition of a user according to the present invention in accordance with a first embodiment.
Figure 5:
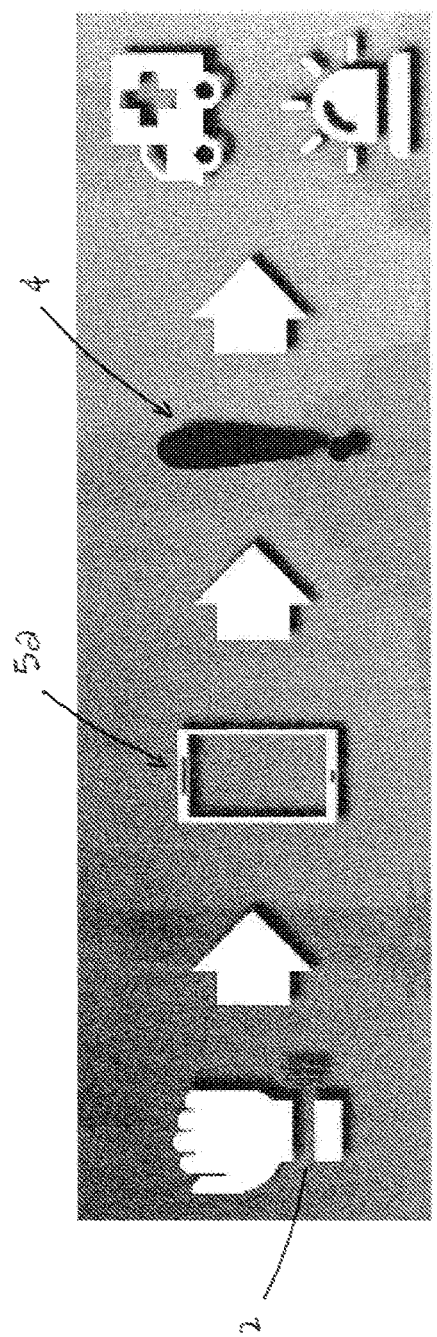
FIG. 5 is a schematic view of a system for monitoring the physical condition of a user according to FIG. 1.

Preferably, in the case of monitoring a single user, the communication device 5 is of the personal type, hence it is a smartphone or a tablet 5a (FIGS. 1 and 5), and the transmission system between the data detection device and the personal communication device 5a operates via the Bluetooth Low Energy (BLE) protocol.

As previously mentioned, the monitoring system 1 object of the present invention can also monitor a plurality of patients, each equipped with at least one data detection device 2.

Figure 6:
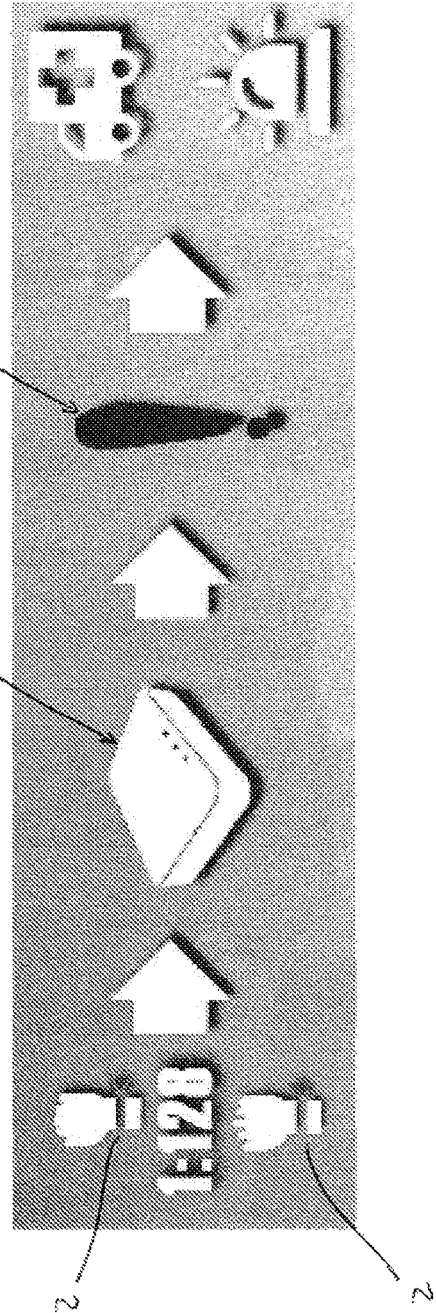
FIG. 6 is a schematic view of a system for monitoring the physical condition of a plurality of users.

In this case, the communication device 5 is advantageously a multiple communication device 5b, such as a control station or station, which communicates with the data acquisition control unit 4 (FIGS. 2 and 6).

The latter is equipped with a console or software or application (app) that enables the vision of one or a plurality of monitored subjects (having permission to do so, via login and password).

Visually, the console present in the server or data acquisition control unit 4 warns if a user is in danger. Downstream of an alarm (for privacy) you can access the user page where you will see: which sensor(s) is/are in alarm, the person's life-saving data, the map with the position marker at the time of the alarm, the route taken in the last hour (a variable ranging from never to always), the sensor data in real time.

In the case of monitoring a plurality of users, each data detection device 2 sends the detected values to the corresponding multiple communication device 5b or station via radio frequency.

The communication device 5 is controlled by a respective software that pre-analyses the data by using the decision-making algorithm that is wired into the source file of the software itself, thereby understanding whether there is a potential alarm state or not. When a potential alarm state is initiated, the software starts data transmission towards the data acquisition control unit 4, sending the data of all the sensors, continuously for a predetermined time interval (for example 2 or 3 minutes), all encrypted. In the case of non-alarm, only the GPS position is sent to the data acquisition control unit 4 at predetermined intervals (e.g. every 3 or 5 minutes). Thus, the GPS is switched on for a preset time at regular intervals (e.g. half a second every 5 minutes) except in the event of an alarm.

The data acquisition control unit 4 is also provided with a database in which the personal data is written in a table suitable to contain it. This table is preferably encrypted. Also in the case of non-alarm, the data acquisition control unit 4 writes with a predetermined frequency, for example every 3 or 5 minutes, the position of the user in a specially dedicated table.

When a potential alarm situation exists, the data acquisition control unit 4 receives the data collection from the software continuously for a few minutes, for example every 2 or 3 minutes. This data is processed following the decision-making algorithm. After the data analysis, the pre-alarm is ended or an alarm is triggered.

In the latter situation, the data acquisition control unit 4 communicates with the operations centre 6 giving it the order to send a pre-recorded call to the default number to contact in case of emergency (ICE), which is part of the data of the monitored subject, which is decrypted only in case of an alarm so as to be used to manage the problem.

The ICE emergency number is dialed anywhere in the world, and a voice recording is sent warning that a monitored person could be in danger. All this is to alert the operations centre or the chosen person to contact in case of emergency in a synchronous and intrusive way, to make sure it/he/she is informed in real time.

To avoid false positives, before the alarm signal is triggered, the server or data acquisition control unit 4 requires a feedback signal after a certain amount of time after receiving the first anomalous value.

For example, the presence sensor, also known as the tear sensor, is used to detect any aggressions or falls: if the data detection device 2 ceases to be present on the skin of the monitored subject, this means that it has been torn off, presumably due to a fall or an aggression. If the absence of the wearable device is detected, before the alarm is sent, the control unit waits for a few seconds and checks the new data transmitted by the data detection device 2. If its presence is detected, then no signal is sent, otherwise a first feedback is sent to the monitored person by means of loud sounds or flashing on the screen of his/her tablet or smartphone. If no feedback is received, the control unit alerts the operations centre 6 that handles the call.

Similar behaviour also for the other sensors, such as the temperature sensor, the plethysmography or heart rate sensor, the three-axis accelerometer sensor (capable of detecting, for example, any falls, number of steps, monitoring movement), etc.

Advantageously, the monitoring system also comprises a button 2d with which the user can request one or more differentiated features on the basis of the duration of the pressure on the button itself.

In particular, the button enables the panic function to be activated, by which the user asks for immediate assistance from the control centre. Other features can be implemented on request.

The two transmission protocols are also due to the fact that the monitoring system must operate both in the open and in closed environments.

It has to be realized that at home or in the office it is preferable not to be dependent on the mobile phone. To this end, it is best to use radio frequency communication protocols and a proprietary cuff. In closed environments, in fact, it is preferable not to use the Bluetooth low energy protocol but to use the radio frequency, which enables operation at a distance of up to 800 m (in open field) between the data detection device 2 and the data acquisition control unit 4. This means that at home or in the office, or anyway in any geographically fixed place, it will be possible to use, instead of a cell phone, an Android on stick equipped with an antenna, an integrated SIM, and that operates by radio frequency and allows a plurality of data detection devices 2 to be connected together (for example to monitor a whole family). It will also be possible to operate at a distance of up to 800 m and have no need of a mobile phone. Lastly, since radio frequency prevails over Bluetooth, the data detection device 2, which has both protocols, when entering the house or wherever there is an Android on stick, will stop transmitting to the cell phone and begin to transmit to the Android on stick i.e. the control station 5b; on the contrary, when exiting the range of the station, it will look for the smartphone with which it is associated, to continue transmitting.

The object of the present invention is also a method for monitoring the physical condition of a user, thus comprising the steps of detecting indicators of the physical condition of the user by means of the data detection device 2, which sends the detected indicators to a data processing device 3 which processes the data received from the data detection device 2 and compares it with a predetermined range of values.

When the received indicators are not within the predetermined range of values, a visual and/or acoustic warning signal is issued to the user and/or a signal is output for the activation of an alarm device.

Within the data processing device 3, the data sent by the data detection device 2 is first analysed by a communication device 5 and subsequently sent to a data acquisition control unit 4, which compares it with the predetermined range of values.

The invention also relates to a method implemented by means of a computer, which allows different algorithms to be carried out, and a computer program configured to implement this method.

Examples of such decision-making algorithms are given below.

EXAMPLE 1: ALGORITHM FLOWCHART IN CASE OF PUSHING OF THE PANIC BUTTON

1. Start
2. Pushing of the panic button for at least 3 seconds by the user
3. Immediate alarm
    a. Feedback to the monitored user via
        i. Loud sounds on the mobile phone
            1. Duration 30 seconds
            2. Unstoppable
            3. Audible even if the mobile phone is muted
                a. It serves the purpose of
                    i. Inducing the attackers to leave
                    ii. Letting the monitored subject know that the call is being taken care of and that help will be given
        ii. Red mobile phone screen with siren logo
4. Call made to the ICE (in case of emergency) number
5. The operations centre calls the monitored user to understand the actual severity;
6. If the monitored user does not need intervention, the alarm stops;
7. In case of need, the OC (Operations Centre) calls the police or the ambulance or the fire brigade
8. End

EXAMPLE 2: ALGORITHM FLOWCHART BRANCH PRESENCE SENSOR

1. Start
2. Presence sensor alarm (i.e. the wearable device has been removed)
3. About 3 seconds are allowed to pass
4. It is checked whether the presence sensor is still in alarm
5. If not, end of alarm 6. If so: Immediate alarm
   a. Feedback to the monitored user via
   i. Loud sounds on the mobile phone
      1. Duration 30 seconds
      2. Unstoppable
      3. Audible even if the mobile phone is muted
         a. It serves the purpose of
            i. Inducing the attackers to leave
            ii. Letting the monitored subject know that the call is being taken care of and that help will be given
      ii. Red mobile phone screen with siren logo
7. Call made to the ICE (in case of emergency) number
8. The operations centre calls the monitored user to understand the actual severity
9. If the monitored user does not need intervention, the alarm stops;
10. In case of need, the OC (Operations Centre) calls the police or the ambulance or the fire brigade
11. End

EXAMPLE 3: ALGORITHM FLOWCHART BRANCH FREE FALL

1. Start
2. Free fall sensor alarm (potential fall)
3. Pre-alarm
   a. Feedback to the monitored user via
   i. Loud sounds on the mobile phone
      1. Stoppable
   b. Audible even if the mobile phone is muted
4. Duration 30 seconds
5. The user stops the pre-alarm by hand through the app
6. End of alarm
7. If he/she does not stop it: Immediate alarm
   a. Feedback to the monitored user via
   i. Loud sounds on the mobile phone
      1. Duration 30 seconds
      2. Unstoppable
      3. Audible even if the mobile phone is muted
         a. It serves the purpose of
            i. Inducing any attackers to leave
            ii. Letting the monitored subject know that the call is being taken care of and that help will be given
      ii. Red mobile phone screen with siren logo
8. Call made to the ICE (in case of emergency) number
9. The operations centre calls the monitored user to understand the actual severity
10. If the monitored user does not need intervention, the alarm stops;
11. In case of need, the OC (Operations Centre) calls the police or the ambulance or the fire brigade
12. End

EXAMPLE 4: ALGORITHM FLOWCHART BRANCH ACCELEROMETER

1. Start
2. Peak accelerometer sensor alarm
3. Data collection from all sensors for 60 seconds
4. It is checked whether the beats are increased by at least 30 after point 2
5. If not, end of alarm
6. If so: it is checked whether the pedometer indicates more than 3 steps taken after point 2
7. If so, end of alarm
8. If not: it is checked whether the movement of the GPS is greater than 30 m after point 2
9. If so, end of alarm
10. If not: Pre-alarm
    a. Feedback to the monitored user via
    i. Loud sounds on the mobile phone
       1. Stoppable
    b. Audible even if the mobile phone is muted
11. Duration 30 seconds
12. The user stops the pre-alarm by hand through the application
13. End of alarm
14. If it is not stopped: Immediate alarm
    a. Feedback to the monitored user via
    i. Loud sounds on the mobile phone
       1. Duration 30 seconds
       2. Unstoppable
       3. Audible even if the mobile phone is muted
          a. It serves the purpose of
             i. Letting the monitored subject know that the call is being taken care of and that help will be given
       ii. Red mobile phone screen with siren logo
15. Call made to the ICE (in case of emergency) number
16. The operations centre calls the monitored user to understand the actual severity
17. If the monitored user does not need intervention, the alarm stops;
18. In case of need, the OC (Operations Centre) calls the police or the ambulance or the fire brigade
19. End

EXAMPLE 5: ALGORITHM FLOWCHART BRANCH HEART RATE

1. Start
2. Heart rate sensor alarm
3. Data collection from all sensors for about 60 seconds
4. It is checked whether the data continues to flow from the wearable device towards the application or the control station or station
5. If so, it is checked whether the heart rate sensor is still in alarm
6. If not, end of alarm
7. If the heart rate sensor is still in alarm or the data does not flow from the wearable device to the application or the station: Immediate alarm
   a. Feedback to the monitored user via
   i. Loud sounds on the mobile phone
      1. Duration 30 seconds
      2. Unstoppable
      3. Audible even if the mobile phone is muted
         a. It serves the purpose of
            i. Inducing the attackers to leave
            ii. Letting the monitored subject know that the call is being taken care of and that help will be given
      ii. Red mobile phone screen with siren logo
8. Call made to the ICE (in case of emergency) number
9. The operations centre calls the monitored user to understand the actual severity
10. If the monitored user does not need intervention, the alarm stops;
11. In case of need, the OC (Operations Centre) calls the police or the ambulance or the fire brigade
12. End

EXAMPLE 6: ALGORITHM FLOWCHART BRANCH SKIN TEMPERATURE

1. Start
2. Skin temperature sensor alarm

3. It is checked whether skin temperature pre-alarms have been sent during the last 60 minutes
4. If so, end of alarm
5. If not: Pre-alarm
   a. Feedback to the monitored user via
   b. Loud sounds on the mobile phone
   c. Stoppable
   d. Audible even if the mobile phone is muted
   e. Duration 30 seconds
6. The user stops the pre-alarm by hand through the application
7. End of alarm
8. If it is not stopped: Immediate alarm
   a. Feedback to the monitored user via
   b. Loud sounds on the mobile phone
   c. Duration 30 seconds
   d. Unstoppable
   e. Audible even if the mobile phone is muted
   i. It serves the purpose of
      1. Inducing the attackers to leave
      2. Letting the monitored subject know that the call is being taken care of and that help will be given
9. Red mobile phone screen with siren logo
10. Call made to the ICE (in case of emergency) number
11. The operations centre calls the monitored user to understand the actual severity
12. If the monitored user does not need intervention, the alarm stops;
13. In case of need, the OC (Operations Centre) calls the police or the ambulance or the fire brigade
14. End The invention allows the achievement of the intended goals.

The above-described monitoring system allows the handling of GPS signals on board a smartphone, tablet or PC and of sensor signals on board wearable devices with the aim of monitoring the user around the clock.

The monitoring that is carried out allows prompt intervention even in the case of immediate danger and/or unconsciousness of the user. In this way, the user does not need to ask for help himself/herself, but he/she can receive rescue regardless of his/her active request.

The system also provides for the possibility of asking for help consciously. The data detection device is of the wearable type, therefore it performs a constant monitoring of the user without the latter having to do anything.

The plurality of sensors possessed by the wearable data detection device allows various functional parameters to be monitored, thus giving a complete picture of the physical and dynamic situation of the user.

The invention claimed is:

1. A monitoring system of the physical condition of at least one user comprising:
   at least one data detection device suitable to detect, by means of sensors, one or more indication data of the physical condition of the user and capable of sending said indication data to a data processing device;
   said data processing device being able to acquire and process the indication data received from said data detection device and able to compare such data with a range of predefined values and emitting an alarm signal when the received indication data do not fall within a range of predefined values;
   wherein the data processing device comprises a data acquisition control unit which sends the alarm signal to an operations center in order to trigger one or more predetermined actions; said operations center activating an alarm device in response to the alarm signal sent by the data acquisition control unit; characterized in that the alarm device emits visual and/or acoustic warning signals to alert the user of an alarm signal and give feedback to the monitored user about the triggering of an alarm that will be handled to prevent any false positive signals that could trigger a rescue without a real reason.

2. The monitoring system according to claim 1, wherein the data processing device comprises a communication device able to send indication data to said data acquisition controller.

3. The monitoring system according to claim 2, wherein the communication device comprises a personal communication device or a multiplex communication device.

4. The monitoring system according to claim 3, wherein the personal communication device comprises a mobile telephone, a computer or a tablet.

5. The monitoring system according to claim 3, wherein the multiplex communication device comprises a control station.

6. The monitoring system according to claim 1, wherein said data detection device communicates with said data processing device via a Bluetooth or radio frequency transmission system.

7. The monitoring system according to claim 1, wherein the data detection device comprises a wearable device having detection sensors in proximity to the user's body; said wearable device having an armband for fastening to the user's body or a clip fastening element suitable to secure the wearable device to a garment worn by the user.

8. The monitoring system according to claim 1, comprising a plurality of data detection devices, each assigned to a respective user, and each of which is suitable to detect, by means of sensors, one or more indication data of the physical condition of its respective user and able to send said indication data to a data processing device, said data processing device being able to acquire and process the indication data received from the data detection devices for each user and able to compare such data with a range of predefined values relating to each individual user, and emitting an alarm signal when the indication data received do not fall within the range of predefined values for that specific user.

9. The monitoring system according to claim 8, wherein the data acquisition controller is equipped with a control console for the simultaneous monitoring of a plurality of users each equipped with at least one said data detection device.

10. A method for monitoring the physical condition of a user comprising the steps of:
   a. detecting indication data of the physical condition of the user by means of a data detection device;
   b. sending of said detected indication data to a data processing device;
   c. processing the data received from the data detection device;
   d. comparing said indication data with a predefined range of values and emitting a warning signal when said received indication data do not fall within the predefined data range;
   e. emitting a visual and/or acoustic warning signal to the user and/or
   f. activation of an alarm device; and
   g. pre-analyzing the indication data via a decisional algorithm to eliminate any false positives in such a way as to send the alarm signal only in case of real danger.

11. The method for monitoring the physical condition of a user according to claim 10, wherein the step of sending said indication data from the data detection device to the data processing device takes place by means of a Bluetooth or radio frequency transmission system.

12. The method for monitoring the physical condition of a user according to claim 10, wherein the indication data produced by the data detection device is first analyzed by a communication device and subsequently sent to a data acquisition controller which compares said indication data with the predefined value range.

13. The method for monitoring the physical condition of a user according to claim 12, wherein the sending of data from the communication device to the data acquisition controller takes place via a signal encryption step.

14. The method for monitoring the physical condition of a user according to claim 10, also comprising a step in which the indication data received by the data processing device is stored in a data storage device.

\* \* \* \* \*